United States Patent [19]

Harris

[11] 4,135,507

[45] Jan. 23, 1979

[54] CONDYLOCEPHALIC NAIL FOR FIXATION OF PERTROCHANTERIC FRACTURES

[76] Inventor: Leslie J. Harris, 340 The Village, #112, Redondo Beach, Calif. 90277

[21] Appl. No.: 798,811

[22] Filed: May 20, 1977

[51] Int. Cl.² .............................................. A61F 5/04
[52] U.S. Cl. .............................. 128/92 BC; 128/92 B
[58] Field of Search ............ 128/92 A, 92 BA, 92 BC, 128/92 B, 92 R, 83

[56] References Cited

U.S. PATENT DOCUMENTS

| | | | |
|---|---|---|---|
| 2,998,007 | 8/1961 | Herzog | 128/92 BC |
| 3,709,218 | 1/1973 | Halloran | 128/92 A |
| 4,055,172 | 10/1977 | Ender et al. | 128/92 BA |

Primary Examiner—John D. Yasko
Attorney, Agent, or Firm—I. Morley Drucker

[57] ABSTRACT

The condylocephalic nail of this invention is designed to attain an optimal nail position in the head-neck fragment of the femur, and, to this end, is provided with a curve as viewed in the frontal or anterior-posterior (AP) plane, which places the upper portion of the nail adjacent to the medial cortex at the level of the lesser trochanter and also places it approximately parallel with the primary trabeculae of the head, i.e., at an included angle of about 160° with respect to the shaft of the femur. The relatively high angle of the upper end of the nail was chosen in order to place it closely parallel to the stress lines encountered by the head and neck of the femur during ambulation. In order to achieve accurate rotatory alignment and to obviate external rotatory malalignment of the femur, the nai is provided, as viewed from the medial side, with a gentle S-shaped curve, in which the upper end or head of the S is formed with an anteversion curve of between about 5°–15° and the remainder, or body portion, of the S-shaped curve is formed with an included anterior-posterior angle of between about 155°–175°. The optimum angle for the S-shaped curve is about 8° for the anteversion portion and about 170° for the included anterior-posterior angle.

13 Claims, 8 Drawing Figures

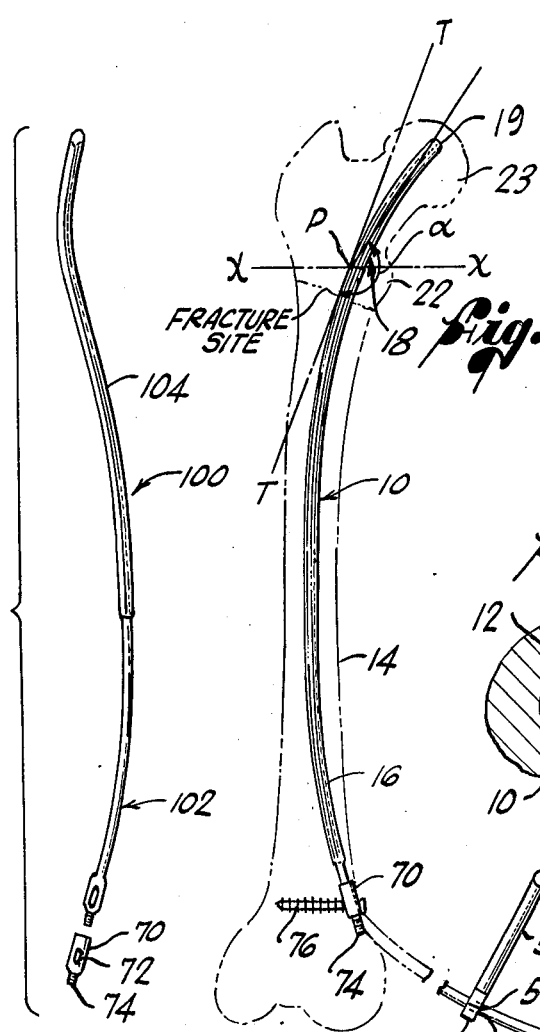

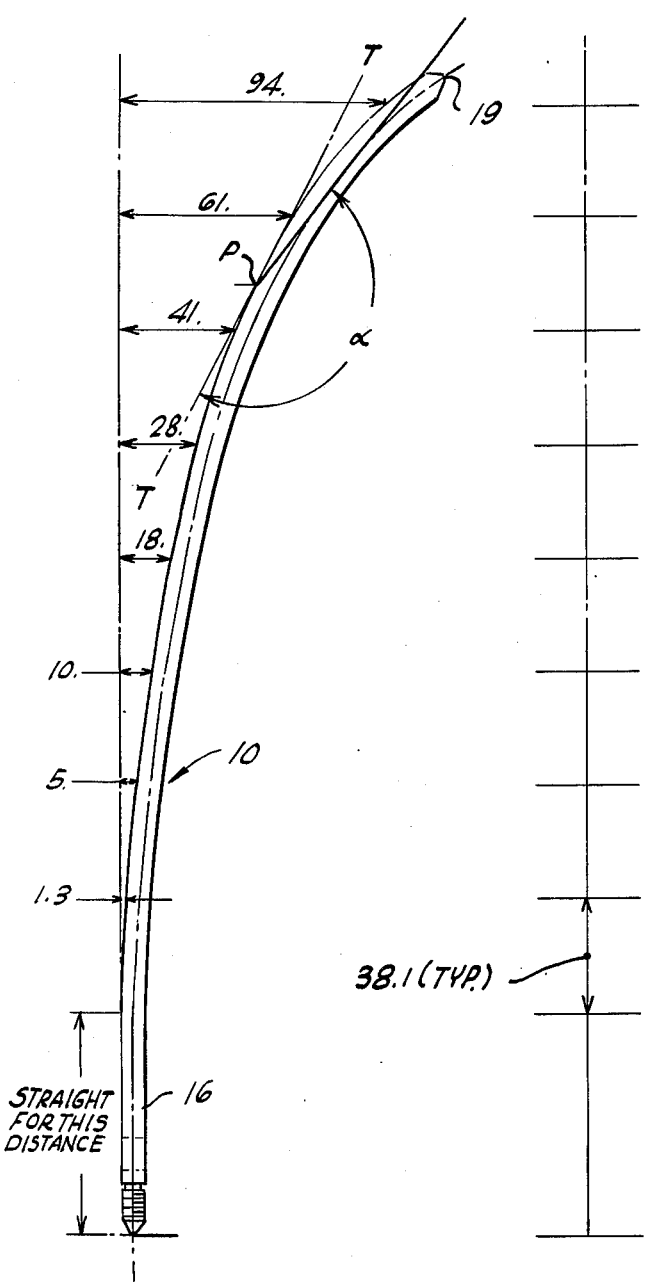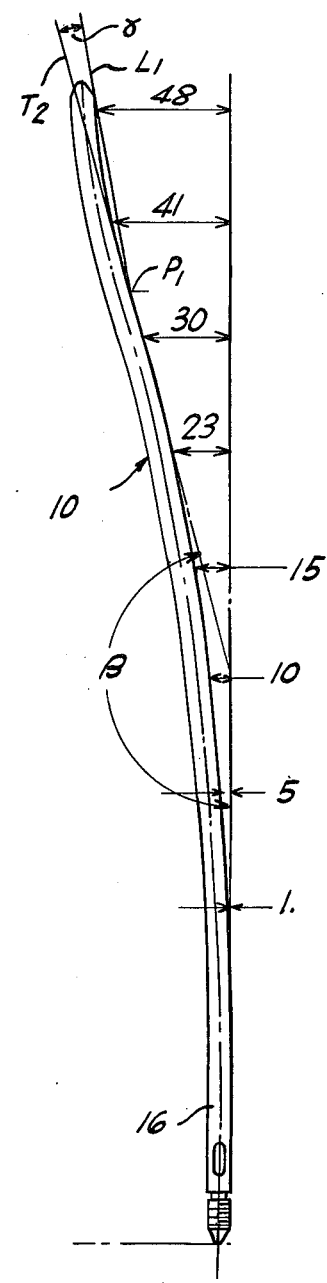

CONDYLOCEPHALIC NAIL FOR FIXATION OF PERTROCHANTERIC FRACTURES

BACKGROUND OF THE INVENTION

Closed condylocephalic nailing of peritrochanteric fractures have been utilized with relatively great success (as compared with open hip nailing procedures). The closed condylocephalic nailing procedure was first introduced by Küntscher in 1966. Küntscher's method consists of the passage of a curved hollow nail with a clover leaf cross-section over a guide pin from the medial femoral condyle into the medullary canal. The nail is driven retrograde across the fracture site into the femoral head. A flat pin is placed through the distal aspect of the nail to theoretically prevent distal migration. An image intensifier and fracture table are required[1].

[1] Küntscher, G.: A New Method of Treatment of Peritrochanteric Fractures, Proc. Roy. Soc. Med., 63:1120-1121, November 1970.

In 1970 Ender reported a similar technique. Three to four 4.5 millimeter flexible pins are inserted above the medial epicondyle into the medullary canal. Ideally the pins are made to diverge in the femoral head[2].

[2] Kuderna, H. Böhler, N., and Collon, D.: Treatment of Intertrochanteric and Subtrochanteric Fractures of the Hip by the Ender Method. J. Bone and Joint Surg. 58-A:604-611 July 1976.

Complications with Küntscher's and Ender's techniques include penetration of the nail(s) through the femoral head, migration of the nail(s) distally interfering with knee function, and a high incidence of external rotation deformities. An accurate estimation of nail length is critically important in both procedures.

The Küntscher nail is relatively rigid and designed with a slight curvature as seen in the anterior-posterior (AP) view of FIG. 1 of the drawings, but is planar as viewed laterally or medially (FIG. 2). Its resultant position in the AP view is most often at the superior-lateral cortex of the neck and head; a comparatively weak area for fixation. Therefore, immediate weight bearing is not recommended in unstable fractures.

The Ender pins are designed with a curvature similar to Küntscher's nail but are much more flexible. Because of the flexibility of the Ender pins, trochanteric osteotomy, through an incision over the hip, is recommended in many stable intertrochanteric fractures. In addition, unstable fractures require additional accessory pins inserted from the lateral femoral condyle. A major complication of this technique is fixation of the fracture in external rotation (noted in 45% of the patients in a recent series using Ender's technique[3].)

[3] See footnote 2.

In view of the foregoing, it is desired to redesign a nail for peritrochanteric fractures using a closed condylocephalic operative technique which would offer the following advantages over the prior art:

(a) the nail should be designed with curvature such that it may be consistently placed in an optimal position in the head-neck fragment of the femur;
(b) there should be minimal danger of nail penetration through the femoral head;
(c) the nail should obviate fixation in rotatory malalignment; and
(d) the nail design should provide a margin of error with respect to the selection of the length of nail to be used.

The condylocephalic nail of this invention has been designed to attain the foregoing objectives. Other advantages resulting from the condylocephalic nail of this invention will become apparent from the summary and detailed description set forth hereafter.

BRIEF DESCRIPTION OF THE DRAWINGS

FIG. 1 is an anterior-posterior (AP) view of the prior art Küntscher condylocephalic nail, shown implanted in a right femur;

FIG. 2 is a medial-lateral view of FIG. 1, taken in the direction of the arrow 2;

FIG. 3 is an AP view of the condylocephalic nail of this invention, as implanted in a right femur;

FIG. 4 is a medial-lateral view of FIG. 3 taken in the direction of the arrow 4;

FIG. 5 is a sectional view of FIG. 4 taken along the line 5—5;

FIG. 6 is a medial-lateral view of a second embodiment of condylocephalic nail of my invention; and FIGS. 7 and 8 are AP and medial-lateral views, respectively, of the condylocephalic nail of my invention showing the specific optimum curves, to scale, of each of the AP and lateral aspects thereof.

SUMMARY OF THE INVENTION

The condylocephalic nail of this invention is designed to attain an optimal nail position in the head-neck fragment of the femur, and, to this end, is provided with a curve as viewed in the frontal or anterior-posterior (AP) plane, which places the upper portion of the nail adjacent to the medial cortex at the level of the lesser trochanter and also places it approximately parallel with the primary trabeculae of the head, i.e., at an included angle of about 160° with respect to the shaft of the femur. The relatively high angle of the upper end of the nail was chosen in order to place it closely parallel to the stress lines encountered by the head and neck of the femur during ambulation.

In order to achieve accurate rotatory alignment and to obviate external rotatory malalignment of the femur, the nail is provided, as viewed from the medial side, with a gentle S-shaped curve, in which the upper end or head of the S is formed with an anteversion curve of between 5–15° and the remainder, or body portion, of the S-shaped curve is formed with an included anterior-posterior angle of between about 155–175°. The optimum angle for the S-shaped curve is about 8° for the anteversion portion and about 170° for the included anterior-posterior angle.

The nail of this invention is made of a flexibly resilient material with a preferably diamond-shaped cross-section, in order to provide sufficient elasticity to be insertable within the wide variety of femoral intermedullary canal diameters and associated head-neck angles, anteversion angles and anterior-posterior angulations. The nail elasticity and section modulus is such as to permit the nail to assume its original curved shape after it has been implanted into the intermedullary canal of the femur.

Nail lengths of various sizes may be employed, along with threadably mounted nail length extenders. The nails and extenders are preferably formed with a slotted distal aperture for easy passage of a cancellous cross-screw thereby providing distal anchorage for the condylocephalic nail.

DETAILED DESCRIPTION OF THE INVENTION

The condylocephalic nail of this invention is designated, generally, by the numeral 10, and is made of a biologically inert, flexibly resilient, strong, material that after implantation in the intermedullary canal 12 of the femur 14 will return to its original shape. The presently preferred material for the nail 10 is a titaniumvanadium-aluminum alloy, such as Titanium 6AL-4 Valloy, mfg. by Zimmer-USA, Warsaw, Indiana, under its mark TIVANIUM.

The nail 10 is preferably formed with a diamond-shaped cross-section measuring on the order of 8 × 11 mm. The material and cross-sectional configuration employed provide sufficient elasticity to accommodate a wide variety of femoral head-neck angles, anterior-posterior angulations, anteversion angles, and medullary canal dimensions found in the general patient population.

Referring now to the AP view of FIG. 3, the curve of the condylocephalic nail is designed so that its proximal end portion 18 provides an included angle of between about 155°-165° measured with respect to the shaft 20 of the femur 14 and optimally about 160°, when viewed in the AP aspect. In order to accomplish this, the nail is provided with a curvature which, at its distal end portion 16, is of large, preferably infinite, radius, the radius of curvature of the nail becoming progressively less as the proximal end portion 18 of the nail 10 is approached.

Short of the proximal tip 19 of the nail 10, and at a point P where the nail 10 intersects the horizontal axis line X—X drawn through the center of the lesser trochanter 22, the included angle α formed between tangent line T—T and the upper proximal portion 18 of the nail 10 is preferably between about 162-172°.

The linear distance between the center of the head 23 of the femur 14 and Point P at the center of the lesser trochanter 22 varies in the general patient population, over a range of between about 60 mm. to about 100 mm. Thus, different sized nails may be employed depending upon the size of the femur, and the linear distance measured from the proximal tip 19 of the nail to the point P will therefore also vary between about 60-100 mm. For purposes of illustration of a single condylocephalic nail example, the distance of point P from the proximal tip 19, in the scale drawing of the AP view, FIG. 7, is 94 mm. and the included angle α is 167°. The nail sizes may vary, preferably, in 5 mm. increments.

While the radius of curvature of the nail 10 becomes progressively smaller from distal end portion 16 to proximal tip 19, this curvature does not follow the curve of a simple mathematical equation. The nature of the curve in the nail 10 is therefore optimally expressed in terms of ever decreasing, but smooth, curvature (measured from the distal end portion) in combination with the presence of a high included angle of between 162°-172° measured from the point P — when the point P is about 60-100 mm. linearly distant from the proximal tip 19 of the nail 10.

An AP curve of the foregoing described characteristics in the nail 10, enables the nail to be placed along the lines of stress of the primary trabiculae, i.e., about 160° ± 5° with respect to the femoral shaft.

The curve of the nail 10, in the medial-lateral view, is also of a complex shape, which does not appear to be expressable in simple mathematical terms. As viewed in the medial-lateral view of FIGS. 4 and 8, the nail is provided with an elongated S-shaped curve having a major fairly uniform, smooth, anterior-posterior curve segment, or major arc 30, commencing at the distal end portion 16 of the nail 10 and continuing proximally to the horizontal line X'—X'. A minor anteversion curve segment or minor arc 32 is then provided in the proximal end portion 18 of nail 10 proximally of the major arc 30, commencing at line X'—X'. The line X'—X' is drawn through the center of the lesser trochanter 22, and lies in the same horizontal plane as line X—X of FIG. 3.

The tangent lines $T_1$ and $T_2$ drawn from the respective ends of the great arc 30 subtends an included angle $\beta$ of between about 155-175°.

The angle $\gamma$ of the anteversion curve segment, or minor arc 32, is defined as follows: first, the angle $\gamma$ is measured at point $P_1$, which is the point of the common tangent of the arcs 30 and 32. (Point $P_1$ is also preferably located on line X'—X', which is the horizontal line through the center of the lesser trochanter 22). The angle between line $L_1$ drawn from the proximal tip 19 of the nail 10 to point $P_1$, together with the upward continuation of tangent line $T_2$ then defines the minor arc by means of the angle $\gamma$.

Angle $\gamma$ has a value of about 5 to 15°. The angles $\beta$ and $\gamma$ are, optimally, about 170° and 8°, respectively.

In the Küntscher and Ender nails, the medial-lateral view is wholly planar. Thus, as the Küntscher and Ender nails are driven up through the intermedullary canal of the femur, as shown in FIG. 1, the nail will rotate internally to accommodate the normal anterior-posterior curvature of the femur. The proximal end of the Küntscher or Ender nail may then lie posterior to the head-neck fragment, as shown in dotted line 50, in FIG. 2, due to the internal rotation and require fixation of the femur in a retroverted or externally rotated position. In fact, as previously noted herein, fixation in external rotation of the femur was noted in almost half of the patients in which the Ender nails were inserted.

The use of the elongated S-shaped curve, in the medial-lateral view, i.e., the incorporation of an anteversion angle $\gamma$ in the proximal portion 18 of the nail, together with the use of anterior-posterior angle $\beta$ in the major distal portion of the curve 30, accommodates the normal curvature of the femur and that of the intermedullary canal in the femur to a much greater extent than can planar nail(s) and has been effective in achieving and maintaining rotatory alignment.

The condylocephalic nail of this invention is easily and consistently placed adjacent to the inferomedial cortex at the intertrochanteric line, and parallel to the primary compressive trabeculae. The resultant load on the femoral head during slow ambulation corresponds to the orientation of the primary compressive trabeculae in the head and neck at an angle of about 160° to the femoral shaft. The loading vectors, therefore, are parallel to the orientation of the nail. The nail is subjected to minimal bending forces and the fracture fragments impact axially about the nail with weight bearing.

The operative technique required to implant the nail 10 of this invention will now be described.

On admission, the patients were placed in Buck's traction and treatment of underlying medical problems immediately begun. All patients received antithrombosis prophylaxis on admission which was continued for two weeks postoperative, or until the patients were ambulatory. Surgery was performed within two (2) to seven (7) days from hospital admission.

After spinal or general anesthesia of the patient, the fracture is reduced under image intensifier control with the patient positioned on the fracture table. A four to five centimeter longitudinal incision is begun two centimeters anterior and one centimeter proximal to the adductor tubercle and continued distally. This distal placement of the incision is necessary to avoid damage to the skin during later passage of the nail. The incision is carried through the interval between the vastus medialis and adductor magnus at the proximal aspect of the wound. A 6.35 millimeter drill bit is used to penetrate the periosteum and medial femoral cortex two centimeters anterior to the adductor tubercle. The hole in the cortex is enlarged with a curved broach (standard). The nail length is determined by placing a nail on the anterior aspect of the thigh, superimposing the proximal end on the femoral head using the image intensifier. The distal end of the nail should ultimately lie at least two centimeters proximal to the insertion site. When there is uncertainty as to which nail length is appropriate, a shorter nail should be selected. Nail extenders as will be described may be used for final adjustment of nail length at the close of the procedure.

The nail 10 is inserted at about 90° to the femoral shaft 14 and allowed to more closely parallel the shaft as it is driven proximally. The distal end of the nail is provided with a threaded end 61 to which is threadably attached the end 65 of a driver extractor 62 (see FIG. 3). The driver-extractor 62 has a handle means 64 (only partially shown) and is used to drive the nail 10 through the intermedullary canal 12 of the femur 14. The anterior-posterior plane of the nail is aligned with the anterior-posterior plane of the femur by using T-bar guide 52, the lower end 54 of which has an opening 56 for passage of the nail therethrough, the upper T-bar end 58 acting as an external guiding means for the nail.

The reduction of the fracture site is confirmed on anterior-posterior and lateral image views of the image intensifier as the nail is driven across the fracture site into the femoral head. Occasionally, reduction in the lateral plane is facilitated by an assistant lifting the proximal thigh anteriorly.

Boyd type III fractures can frequently be reduced in valgus by abducting the leg and pushing medially against the proximal thigh. Traction is then released and the foot plate pushed proximally to impact the fracture.

The distal end of the nail is provided with an elongated aperture or slot 66, as best seen in FIG. 4, which slot is located just proximally of the threaded end 61 of the nail 10. After the nail is tapped to within one centimeter of the subchondral cortex of the femoral head, a cross-screw is passed through the slot 66 and into the medial cortex through the slot perpendicular to the femoral shaft. Engagement of the opposite cortex is not necessary.

In order to facilitate the location of slot 66 after implantation of the nail into the femur, a drill guide 69 is affixed to the driver-extractor 62 (see FIG. 3). The drill guide has an opening 71 formed therein, the central axis B—B thereof accurately aligning a cross-screw with the slot 66.

After the cross-screw has been placed, the deep fascia, subcutaneous tissue and skin are closed in layers and a light compressive dressing is placed above the knee.

In the event that the nail selected is too short for the femur, it may be readily extended, in incremental fashion, before affixation of the cross-section.

Nail extension means 70 are provided which have an internally threaded portion 70a adapted for threadable engagement with the threaded distal end of the nail 10, as shown in FIGS. 3 and 4. The nail extender 70 is provided with a slotted opening 72, and terminates in a threaded end 74. (See also FIG. 6). Nail extenders may, of course, be provided in varying lengths.

A nail extender 70 of appropriate length is added to an undersized nail 10, by first slightly extracting the nail 10 from the femur 14 to expose the threaded end 61 thereof. The nail extender 70 is then threadably mounted thereof and re-driven into the femur 14 to the required depth. A cross-screw 76 may then be driven through the aperture 72 of the nail extender 70, as heretofore described with reference to the nail 10 itself.

The entire operative procedure is usually accomplished in an average of thirty minutes for intertrochanteric fractures, and 65 minutes for subtrochanteric fractures. Blood loss has been negligible in all closed condylocephalic procedures undertaken.

Assessments were made of fracture healing or union on X-Ray, ambulatory status, and hip motion of 84 patients at a median follow-up of eleven months.

Fracture Union: Criteria for fracture union included lack of pain, presence of callus, and obliteration of the fracture on X-Ray. With intertrochanteric and Boyd type III fractures significant callus was usually present at four to six weeks postoperative. Fracture union was judged to have occurred at an average of eleven weeks. One Boyd type III fracture united with 10° of varus settling. Since no limitation in function or hip motion resulted this was not considered a complication. The eight distal subtrochanteric fractures were considered united at an average of eighteen weeks. There were no implant failures, delayed union, nonunions, superficial or deep wound infections. No re-operations were required.

Ambulatory Function: Of the nine patients who were minimally nonambulatory pre-fracture, two were totally bedridden and the remainder required assistance for wheelchair transfers at late follow-up. All of the patients who were household or community ambulators prior to their fracture regained their previous ambulatory status.

Hip Motion: A comparison of hip range of motion was made between the involved and uninvolved sides and shows no significant loss of motion in the involved sides, and, in particular, no evidence of rotatory malalignment was seen.

In summary, the nail of this invention offers the following advantages over the prior art:

1. The nail is consistently placed in an optimal position in the head-neck fragment.
2. There is no requirement for trochanteric osteotomy or accessory fixation in intertrochanteric fractures, and immediate weight bearing is to be encouraged.
3. A margin of error is available in the selection of the length of nail to be used. The appropriately sized nail extender is easily attached to correct the final position of the distal end of the nail. The cross screw has been effective in preventing late "working out" of the nail, although it has allowed settling of the nail with fracture impaction.
4. There have been no cases of nail penetration through the femoral head.
5. The modified nail has obviated fixation in rotatory malalignment.

The nature of the nail material employed is important. It is best described as of a flexibly resilient nature — for as the nail 10 of, complex curvature, is driven through the medullary canal 12, it will be flexed and bent from its original shape but on attainment of its final position, it returns essentially to its original curvature.

The nail of this invention is best described, in broad terms, as being an elongated unitary nail member, made of flexibly resilient material, for condylocephalic insertion and implantion within the femur. The nail member has:

(a) in the anterior-posterior view a radius of curvature that is non-uniform and has further an included angle in a first proximal end portion of said member subtended by
 (i) a tangent line T—T to the nail member, taken at a point P in said first proximal end portion of the nail member, and by
 (ii) a line drawing from said point P to the proximal tip of the nail member
 of between about 162°–172° and (b) in the medial lateral view an S-shaped curve comprising a minor anteversion arcuate curvature extending over a second proximal end portion measured from proximal tip 19 to point $P_1$ of the nail member and a major anterior-posterior arcuate curvature extending over the remaining portion of the nail member.

Points P and $P_1$ may lie on the same horizontal plane or they may be in slightly differing horizontal planes. The S-shaped curve, in medial-lateral view, approximates the shape of the intermedullary canal of the femur.

FIG. 6 illustrates another embodiment of this invention wherein the cross-sectional configuration of the nail 100 is circular in the distal portion 102, and is provided with a diamond-shaped cross-section (as in FIG. 5) in a proximal portion 104. The nail curvature in both the medial-lateral view of FIG. 6, and the AP view (not shown) are the same as heretofore described. Other cross-sectional configurations may also be employed.

Other modifications of this invention will occur to those skilled in the art. I therefore intend to be bound only by the claims which follow.

I claim:

1. An elongated unitary member, made of flexibly resilient material, for condylocephalic insertion and implantation within the intramedullary canal of the femur, said member having:
 (a) in the anterior-posterior view a radius of curvature that is non-uniform and having further an included angle in a first proximal end portion of said member subtended by
  (i) a tangent line to said member, taken at a point P in said first proximal end portion of said member, and by
  (ii) a line drawn from said point P to the proximal tip of said member
  of between about 162°–172° and
 (b) in the medial-lateral view an S-shaped curve comprising a minor anteversion arcuate curvature extending over a second proximal end portion of said member and a major anterior-posterior arcuate curvature extending over the remaining portion of said member.

2. The unitary member of claim 1 wherein in the anterior-posterior view said radius of curvature decreases progressively from the distal end portion of said member to its proximal tip.

3. The unitary member of claim 1 wherein said first proximal end portion and said second proximal end portion are coextensive.

4. The unitary member of claim 1 wherein said first proximal end portion and said second proximal end portion have differing lengths.

5. The unitary member of claim 1 wherein said included angle is about 167°.

6. The unitary member of claim 1 wherein the linear distance of said first proximal end portion and said second proximal end portion is equal to a value of between 60 and 100 mm.

7. The unitary member of claim 1 wherein in the anterior-posterior view said radius of curvature decreases progressively from the distal end portion of said member to its proximal tip, the distal end portion terminating distally in a straight portion.

8. The unitary member of claim 1 wherein said member is provided with a threaded distal tip, and an aperature proximally adjacent thereto.

9. The unitary member of claim 1 wherein said member has attached thereto a second extender member having a threaded tip and an aperature proximally adjacent thereto.

10. The unitary member of claim 1 wherein the major anterior-posterior arcuate curvature of said S-shaped curvature generally follows the shape of the intermedullary canal of the shaft of a normal femur.

11. The unitary member of claim 1 wherein the major posterior-anterior curvature of said S-shaped curvature has a fairly uniform, radius of curvature, the intersecting tangent lines from the ends of said major posterior-anterior curvature subtending an angle of between about 155–175°.

12. The unitary member of claim 1 wherein the minor anteversion arcuate curvature extending over said second proximal end portion is defined by an angle of between 5–15° subtended by (i) a tangent line drawn from the point $P_1$ of the common tangent of the minor and major curvatures of said S-shaped curve and (ii) a line drawn from the proximal tip of said member to said point $P_1$.

13. The member of claim 12 wherein said angle is about 8°.

* * * * *